US011131733B2

(12) United States Patent
Jiang et al.

(10) Patent No.: US 11,131,733 B2
(45) Date of Patent: Sep. 28, 2021

(54) SYSTEM AND METHOD FOR MAGNETIC RESONANCE FINGERPRINTING WITH NON-LOCALLY SEQUENTIAL SAMPLING OF K-SPACE

(71) Applicants: Case Western Reserve University, Cleveland, OH (US); Siemens Healthcare GmbH, Erlangen (DE)

(72) Inventors: Yun Jiang, Cleveland, OH (US); Mark A. Griswold, Shaker Heights, OH (US); Gregor Korzdorfer, Erlangen (DE); Mathias Nittka, Erlangen (DE)

(73) Assignees: Case Western Reserve University, Cleveland, OH (US); Siemens Healthcare GmbH, Erlangen (DE)

( * ) Notice: Subject to any disclaimer, the term of this patent is extended or adjusted under 35 U.S.C. 154(b) by 0 days.

(21) Appl. No.: 16/859,175

(22) Filed: Apr. 27, 2020

(65) Prior Publication Data
US 2020/0341092 A1 Oct. 29, 2020

Related U.S. Application Data

(60) Provisional application No. 62/838,772, filed on Apr. 25, 2019.

(51) Int. Cl.
*G01R 33/50* (2006.01)
*G01R 33/56* (2006.01)
(Continued)

(52) U.S. Cl.
CPC .............. *G01R 33/50* (2013.01); *A61B 5/055* (2013.01); *G01R 33/482* (2013.01);
(Continued)

(58) Field of Classification Search
CPC .. G01R 33/50; G01R 33/5608; G01R 33/482; G01R 33/5615; G01R 33/543; A61B 5/055
See application file for complete search history.

(56) References Cited

U.S. PATENT DOCUMENTS 8,723,518 B2  5/2014  Seiberlich
10,261,154 B2  4/2019  Griswold
(Continued)

OTHER PUBLICATIONS

Asslander J, et al. Low rank alternating direction method of multipliers reconstruction for MR fingerprinting. Magn Reson Med. 2018;79(1):83-9.
(Continued)

*Primary Examiner* — G. M. A Hyder
(74) *Attorney, Agent, or Firm* — Quarles & Brady LLP

(57) ABSTRACT

A system and method is provided for acquisition of magnetic resonance fingerprinting ("MRF") data that includes determining a non-locally sequential sampling pattern for a Cartesian grid of k-space, performing a series of sequence blocks using acquisition parameters that vary between sequence blocks to acquire MRF data from a subject using the Cartesian grid of k-space and the determined non-locally sequential sampling pattern, assembling the MRF data into a series of signal evolutions, comparing the series of signal evolutions to a dictionary of known signal evolutions to determine tissue properties of the subject, and generating a report indicating the tissue properties of the subject.

14 Claims, 5 Drawing Sheets

(51) Int. Cl.
- *A61B 5/055* (2006.01)
- *G01R 33/48* (2006.01)
- *G01R 33/561* (2006.01)
- *G01R 33/54* (2006.01)

(52) U.S. Cl.
CPC ....... *G01R 33/543* (2013.01); *G01R 33/5608* (2013.01); *G01R 33/5615* (2013.01)

(56) References Cited

U.S. PATENT DOCUMENTS

| | | | | |
|---|---|---|---|---|
| 2015/0192654 A1* | 7/2015 | Zhu | .................... | G01R 33/5611 324/309 |
| 2018/0106876 A1* | 4/2018 | Nielsen | .................. | G01R 33/50 |
| 2018/0292492 A1* | 10/2018 | Griswold | ......... | G01R 33/34092 |

OTHER PUBLICATIONS

Beck A. et al, A Fast Iterative Shrinkage—Thresholding Algorithm for Linear Inverse Problems. SIAM J Imaging Sci 2009, 2(1):183-202.

Cloos, M.; et al. Multiparametric Imaging with Heterogeneous Radiofrequency Fields. Nature communications 2016; 7:12445.

Cohen O, et al. MR fingerprinting Deep RecOnstruction NEtwork (DRONE). Magn Reson Med. 2018;80:885-894.

Gold GE, et al. Musculoskeletal MRI at 3.0 T: Relaxation Times and Image Contrast. American Journal of Roentgenology 2004 183:2, 343-351.

Hamilton, J. I., et al. Low Rank Compressed Sensing Reconstruction for More Precise Cardiac MRF Measurement. ISMRM 2017 #554.

Jiang Y, et al. MR fingerprinting using fast imaging with steady state precession (FISP) with spiral readout. Magnetic resonance in medicine 2015;74(6):1621-1631.

Keenan K, et al. Comparison of t1 measurement using ISMRM/NIST system phantom. In Proceedings of the 24th Annual Meeting of ISMRM, Singapore, 2016. Abstract 3290.

Liaoc C, et al. 3D MR fingerprinting with accelerated stack-of-spirals and hybrid sliding-window and GRAPPA reconstruction. NeuroImage 2017;162:13-22.

Ma, D, et al. "Fast 3D magnetic resonance fingerprinting for a whole-brain coverage." Magnetic resonance in medicine 79.4 (2018): 2190-2197.

Ma, D. et al., "Magnetic Resonance Fingerprinting," Nature, 2013; 495 (7440): 187-192.

McGivney, D. F., et al. (2014). SVD compression for magnetic resonance fingerprinting in the time domain. IEEE transactions on medical imaging, 33(12), 2311-22.

Pineda, A. R., et al. (2005), Cramér—Rao bounds for three-point decomposition of water and fat. Magn. Reson. Med., 54:625-635.

Rieger, B., et al. (2017), Magnetic resonance fingerprinting using echo-planar imaging: Joint quantification of T1 and T2* relaxation times. Magn. Reson. Med, 78: 1724-1733.

Tamir, J. I., et al. T2 shuffling: Sharp, multicontrast, volumetric fast spin-echo imaging. Magn. Reson. Med.,2017; 77: 180-195.

Zhao B., et al. Improved magnetic resonance fingerprinting reconstruction with low-rank and subspace modeling. Magn. Reson. Med., 2018;79: 933-942.

* cited by examiner

SYSTEM AND METHOD FOR MAGNETIC RESONANCE FINGERPRINTING WITH NON-LOCALLY SEQUENTIAL SAMPLING OF K-SPACE

CROSS-REFERENCE TO RELATED APPLICATIONS

This application claims the benefit of U.S. Provisional Patent Application Ser. No. 62/838,772, filed on Apr. 25, 2019, and entitled "System and Method for Magnetic Resonance Fingerprinting with Non-Sequential Sampling of k-Space," which is incorporated herein by reference as if set forth in its entirety for all purposes.

STATEMENT REGARDING FEDERALLY SPONSORED RESEARCH

This invention was made with government support under 1R01EB016728-01A1, and 5R01EB017219-02 awarded by National Institute of Health. The government has certain rights in the invention.

BACKGROUND

Characterizing tissue species using nuclear magnetic resonance ("NMR") can include identifying different properties of a resonant species (e.g., T1 spin-lattice relaxation, T2 spin-spin relaxation, proton density). Other properties like tissue types and super-position of attributes can also be identified using NMR signals. These properties and others may be identified simultaneously using magnetic resonance fingerprinting ("MRF"), which is described, as one example, by D. Ma, et al., in "Magnetic Resonance Fingerprinting," Nature, 2013; 495(7440):187-192.

Conventional magnetic resonance imaging ("MRI") pulse sequences include repetitive similar preparation phases, waiting phases, and acquisition phases that serially produce signals from which images can be made. The preparation phase determines when a signal can be acquired and determines the properties of the acquired signal. For example, a first pulse sequence may produce a T1-weighted signal at a first echo time ("TE"), while a second pulse sequence may produce a T2-weighted signal at a second TE. These conventional pulse sequences typically provide qualitative results where data are acquired with various weightings or contrasts that highlight a particular parameter (e.g., T1 relaxation, T2 relaxation).

When magnetic resonance ("MR") images are generated, they may be viewed by a radiologist and/or surgeon who interprets the qualitative images for specific disease signatures. The radiologist may examine multiple image types (e.g., T1-weighted, T2-weighted) acquired in multiple imaging planes to make a diagnosis. The radiologist or other individual examining the qualitative images may need particular skill to be able to assess changes from session to session, from machine to machine, and from machine configuration to machine configuration.

Unlike conventional MRI, MRF employs a series of varied sequence blocks that simultaneously produce different signal evolutions in different resonant species (e.g., tissues) to which the radio frequency ("RF") is applied. The signals from different resonant tissues will, however, be different and can be distinguished using MRF. The different signals can be collected over a period of time to identify a signal evolution for the volume. Resonant species in the volume can then be characterized by comparing the signal evolution to known evolutions. Characterizing the resonant species may include identifying a material or tissue type, or may include identifying MR parameters associated with the resonant species. The "known" evolutions may be, for example, simulated evolutions calculated from physical principles and/or previously acquired evolutions. A large set of known evolutions may be stored in a dictionary. In this regard, MRF is a quantitative imaging technique that can estimate multiple tissue properties simultaneously.

Most MRF methods have utilized non-Cartesian sampling patterns, such as spiral, radial, rosette, and stack-of-spirals for 3D, as well as echo planar imaging ("EPI") based pulse sequence to accelerate the acquisition. While these trajectories sample k-space efficiently, they are susceptible to imperfections of the imaging gradients and off-resonance effects. Thus, the resulting signal evolutions acquired in the face of these gradient imperfections or off-resonance effects can include artifacts that can complicate the dictionary matching process.

Thus, it would be desirable to have systems and methods that enable efficient or accelerated acquisitions, without the data being susceptible to gradient imperfections, off-resonance effects, or similar imperfections that can plague non-Cartesian sampling strategies.

SUMMARY OF THE DISCLOSURE

The present disclosure addresses the aforementioned drawbacks by providing a system and method for acquisition of magnetic resonance fingerprinting ("MRF") data using sampling locations that align across a Cartesian grid but are not required to be locally or sequentially sampled. Using the sampling strategies described herein, systems and methods are provided that overcome the negative implications of using traditional Cartesian sampling, such as reduced speeds, while not suffering from the aforementioned drawbacks of non-Cartesian sampling. In some configurations, the systems and methods may use a random or pseudorandom sampling within a Cartesian architecture and/or include temporal low-rank and subspace modeling to achieve T1, T2, and off-resonance quantification using the MRF framework.

In one configuration, a method for magnetic resonance fingerprinting (MRF) data acquisition using a computer system is provided. The method includes determining a non-locally sequential sampling pattern for a Cartesian grid of k-space using the computer system. The method also includes performing a series of sequence blocks using acquisition parameters that vary between sequence blocks to acquire MRF data from a subject using the Cartesian grid of k-space and the non-locally sequential sampling pattern, and assembling the MRF data into a series of signal evolutions. The method also includes comparing the series of signal evolutions to a dictionary of known signal evolutions to determine tissue properties of the subject and generating a report indicating the tissue properties of the subject.

In one configuration, a magnetic resonance fingerprinting (MRF) system is provided, including a magnet system configured to generate a polarizing magnetic field about at least a portion of a subject, a magnetic gradient system including a plurality of magnetic gradient coils configured to apply at least one magnetic gradient field to the polarizing magnetic field, and a radio frequency (RF) system configured to apply an RF field to the subject and to receive magnetic resonance signals from the subject using a coil array. The MRF system also includes a computer system programmed to determine a non-locally sequential sampling pattern for a Cartesian grid of k-space and control the magnetic gradient system and the RF system to perform a series of sequence blocks using acquisition parameters that vary between sequence blocks to acquire MRF data from a subject using the Cartesian grid of k-space and the non-locally sequential sampling pattern; assemble the MRF data into a series of signal evolutions. The computer system is further programmed to compare the series of signal evolutions to a dictionary of known signal evolutions to determine tissue properties of the subject and generate a report indicating the tissue properties of the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Figure 1:
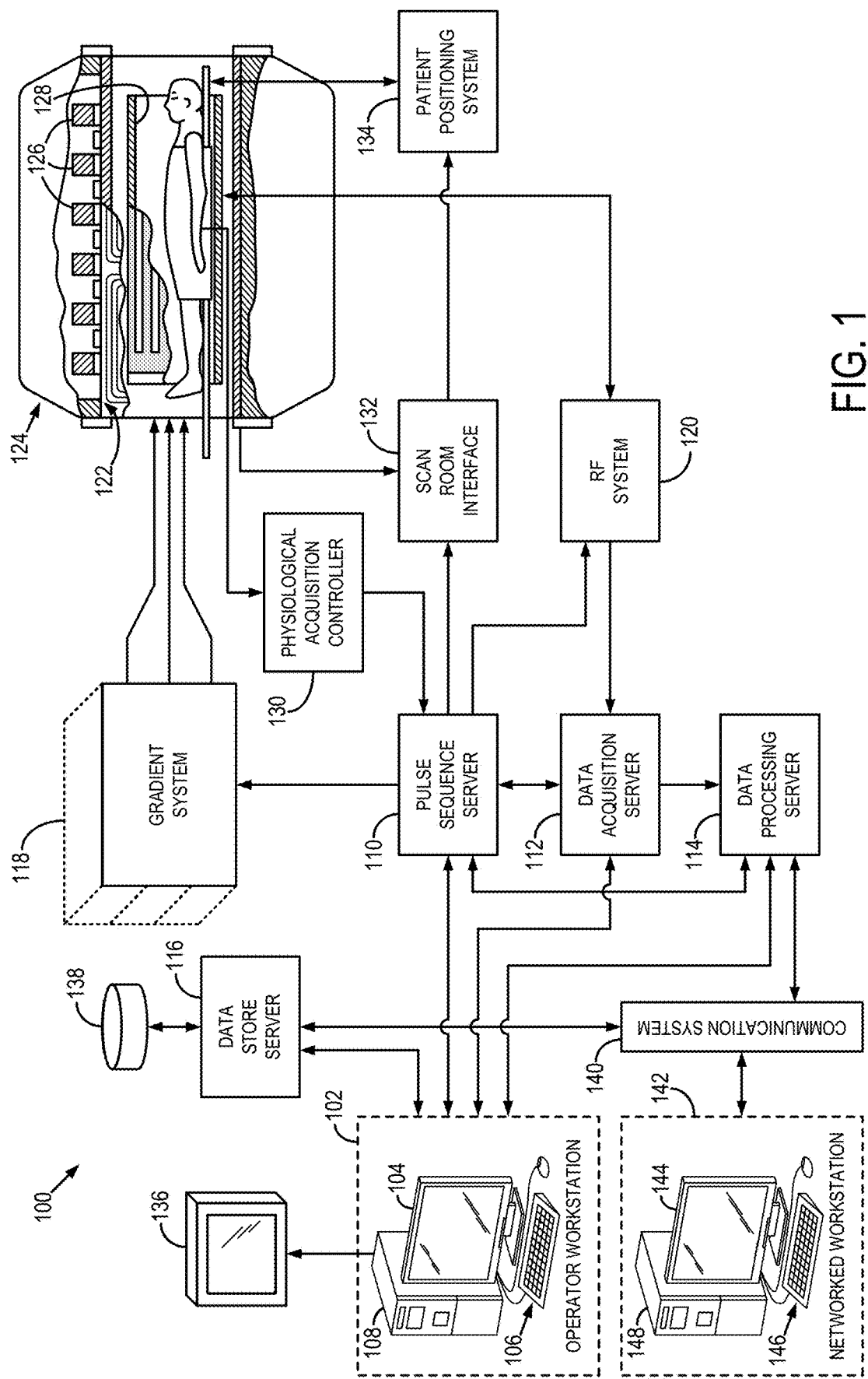
FIG. 1 is a block diagram of an example magnetic resonance imaging ("MRI") system that can implement the methods described in the present disclosure.

Referring to FIG. 1, an example of a nuclear magnetic resonance ("NMR") or magnetic resonance imaging ("MRI") system 100 that can implement the methods described here is illustrated. The MRI system 100 includes a computer system forming an operator workstation 102 that may include a display 104, one or more input devices 106 (e.g., a keyboard, a mouse), and a processor 108. The processor 108 may include a commercially available programmable machine running a commercially available operating system. The operator workstation 102 provides an operator interface that facilitates entering scan parameters into the MRI system 100. The operator workstation 102 may be coupled to different servers, including, for example, a pulse sequence server 110, a data acquisition server 112, a data processing server 114, and a data store server 116. The operator workstation 102 and the servers 110, 112, 114, and 116 may be connected via a communication system 140, which may include wired or wireless network connections.

The pulse sequence server 110 functions in response to instructions provided by the operator workstation 102 to operate a gradient system 118 and a radiofrequency ("RF") system 120. Gradient waveforms for performing a prescribed scan are produced and applied to the gradient system 118, which then excites gradient coils in an assembly 122 to produce the magnetic field gradients $G_x$, $G_y$, and $G_z$ that are used for spatially encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil to perform the prescribed magnetic resonance pulse sequence. Responsive magnetic resonance signals detected by the RF coil 128, or a separate local coil, are received by the RF system 120. The responsive magnetic resonance signals may be amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the prescribed scan and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. An RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at a sampled point by the square root of the sum of the squares of the I and Q components:

$$M=\sqrt{I^2+Q^2} \qquad (1);$$

and the phase of the received magnetic resonance signal may also be determined according to the following relationship:

$$\varphi = \tan^{-1}\left(\frac{Q}{I}\right). \qquad (2)$$

The pulse sequence server 110 may receive patient data from a physiological acquisition controller 130. By way of example, the physiological acquisition controller 130 may receive signals from a number of different sensors connected to the patient, including electrocardiograph ("ECG") signals from electrodes, or respiratory signals from a respiratory bellows or other respiratory monitoring devices. These signals may be used by the pulse sequence server 110 to synchronize, or "gate," the performance of the scan with the subject's heart beat or respiration.

The pulse sequence server 110 may also connect to a scan room interface circuit 132 that receives signals from various sensors associated with the condition of the patient and the magnet system. Through the scan room interface circuit 132, a patient positioning system 134 can receive commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, so that data is not lost by data overrun. In some scans, the data acquisition server 112 passes the acquired magnetic resonance data to the data processor server 114. In scans that require information derived from acquired magnetic resonance data to control the further performance of the scan, the data acquisition server 112 may be programmed to produce such information and convey it to the pulse sequence server 110. For example, during pre-scans, magnetic resonance data may be acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also process magnetic resonance signals used to detect the arrival of a contrast agent in a magnetic resonance angiography ("MRA") scan. For example, the data acquisition server 112 may acquire magnetic resonance data and processes it in real-time to produce information that is used to control the scan.

The data processing server 114 receives magnetic resonance data from the data acquisition server 112 and processes the magnetic resonance data in accordance with instructions provided by the operator workstation 102. Such processing may include, for example, reconstructing two-dimensional or three-dimensional images by performing a Fourier transformation of raw k-space data, performing other image reconstruction algorithms (e.g., iterative or backprojection reconstruction algorithms), applying filters to raw k-space data or to reconstructed images, generating functional magnetic resonance images, or calculating motion or flow images.

Images reconstructed by the data processing server 114 are conveyed back to the operator workstation 102 for storage. Real-time images may be stored in a data base memory cache, from which they may be output to operator display 102 or a display 136. Batch mode images or selected real time images may be stored in a host database on disc storage 138. When such images have been reconstructed and transferred to storage, the data processing server 114 may notify the data store server 116 on the operator workstation 102. The operator workstation 102 may be used by an operator to archive the images, produce films, or send the images via a network to other facilities.

The MRI system 100 may also include one or more networked workstations 142. For example, a computer system forming a networked workstation 142 may include a display 144, one or more input devices 146 (e.g., a keyboard, a mouse), and a processor 148. The networked workstation 142 may be located within the same facility as the operator workstation 102, or in a different facility, such as a different healthcare institution or clinic.

The networked workstation 142 may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may be exchanged between the data processing server 114 or the data store server 116 and the networked workstations 142, such that the data or images may be remotely processed by a networked workstation 142.

The above-described system can be used to perform a magnetic resonance fingerprinting ("MRF") process in accordance with the present disclosure. MRF is a technique that facilitates determining and mapping of tissue or other material properties based on measurements of the subject or object being imaged. In particular, MRF can be conceptualized as employing a series of varied "sequence blocks" that simultaneously produce different signal evolutions in different "resonant species" to which the RF is applied. The term "resonant species," as used herein, refers to a material, such as water, fat, bone, muscle, soft tissue, and the like, that can be made to resonate using NMR. By way of illustration, when radio frequency ("RF") energy is applied to a volume that has both bone and muscle tissue, then both the bone and muscle tissue will produce a nuclear magnetic resonance ("NMR") signal; however, the "bone signal" represents a first resonant species and the "muscle signal" represents a second resonant species, and thus the two signals will be different. These different signals from different species can be collected simultaneously over a period of time to collect an overall "signal evolution" for the volume.

The measurements obtained in MRF techniques are achieved by varying the acquisition parameters from one repetition time ("TR") period to the next, which creates a time series of signals with varying contrast. Examples of acquisition parameters that can be varied include flip angle ("FA"), RF pulse phase, TR, echo time ("TE"), and sampling patterns, such as by modifying one or more readout encoding gradients. In some cases the varied acquisition parameters may be varied in a random manner, pseudorandom manner, or other pattern or manner that results in signals from different materials or tissues to be spatially incoherent, temporally incoherent, or both. For example, in some instances, the acquisition parameters can be varied according to a non-random or non-pseudorandom pattern that otherwise results in signals from different materials or tissues to be spatially incoherent, temporally incoherent, or both.

From these measurements, which may contain signals from different materials or tissues that are spatially incoherent, temporally incoherent, or both, MRF processes can be designed to map any of a wide variety of parameters. Examples of such parameters that can be mapped may include, but are not limited to, longitudinal relaxation time ($T_1$), transverse relaxation time ($T_2$), main or static magnetic field map ($B_0$), and proton density ($\rho$). MRF is generally described in U.S. Pat. Nos. 8,723,518 and 10,261,154, each of which is incorporated herein by reference in its entirety.

The data acquired with MRF techniques are compared with a dictionary of signal models, or templates, that have been generated for different acquisition parameters from magnetic resonance signal models, such as Bloch equation-based physics simulations. This comparison allows estimation of the physical parameters, such as those mentioned above. As an example, the comparison of the acquired signals to a dictionary can be performed using any suitable matching or pattern recognition technique. The parameters for the tissue or other material in a given voxel are estimated to be the values that provide the best signal template matching. For instance, the comparison of the acquired data with the dictionary can result in the selection of a signal vector, which may constitute a weighted combination of signal vectors, from the dictionary that best corresponds to the observed signal evolution. The selected signal vector includes values for multiple different quantitative parameters, which can be extracted from the selected signal vector and used to generate the relevant quantitative parameter maps.

The stored signals and information derived from reference signal evolutions may be associated with a potentially very large data space. The data space for signal evolutions can be partially described by:

$$SE = \sum_{s=1}^{N_S} \prod_{i=1}^{N_A} \sum_{j=1}^{N_{RF}} R_i(\alpha) R_{RF_{ij}}(\alpha, \phi) R(G) E_i(T_1, T_2, D) M_0; \quad (3)$$

where SE is a signal evolution; $N_S$ is a number of spins; $N_A$ is a number of sequence blocks; $N_{RF}$ is a number of RF pulses in a sequence block; $\alpha$ is a flip angle; $\phi$ is a phase angle; $R_i(\alpha)$ is a rotation due to off resonance; $R_{RF_{ij}}(\alpha,\phi)$ is a rotation due to RF differences; $R(G)$ is a rotation due to a magnetic field gradient; $T_1$ is a longitudinal, or spin-lattice, relaxation time; $T_2$ is a transverse, or spin-spin, relaxation time; D is diffusion relaxation; $E_i(T_1,T_2,D)$ is a signal decay due to relaxation differences; and $M_0$ is the magnetization in the default or natural alignment to which spins align when placed in the main magnetic field.

While $E_i(T_1,T_2,D)$ is provided as an example, in different situations, the decay term, $E_i(T_1,T_2,D)$, may also include additional terms, $E_i(T_1,T_2,D, \ldots)$ or may include fewer terms, such as by not including the diffusion relaxation, as $E_i(T_1,T_2)$ or $E_i(T_1,T_2, \ldots)$. Also, the summation on "j" could be replace by a product on "j".

The dictionary may store signals described by, $$S_i = R_i E_i(S_{i-1}) \quad (4)$$

where $S_0$ is the default, or equilibrium, magnetization; $S_i$ is a vector that represents the different components of magnetization, $M_x$, $M_y$, and $M_z$ during the $i^{th}$ acquisition block; $R_i$ is a combination of rotational effects that occur during the $i^{th}$ acquisition block; and $E_i$ is a combination of effects that alter the amount of magnetization in the different states for the $i^{th}$ acquisition block. In this situation, the signal at the $i^{th}$ acquisition block is a function of the previous signal at acquisition block (i.e., the $(i-1)^{th}$ acquisition block). Additionally or alternatively, the dictionary may store signals as a function of the current relaxation and rotation effects and of previous acquisitions. Additionally or alternatively, the dictionary may store signals such that voxels have multiple resonant species or spins, and the effects may be different for every spin within a voxel. Further still, the dictionary may store signals such that voxels may have multiple resonant species or spins, and the effects may be different for spins within a voxel, and thus the signal may be a function of the effects and the previous acquisition blocks.

As described above, data acquired with an MRF technique generally includes data containing random measurements, pseudorandom measurements, or measurements obtained in a manner that results in spatially incoherent signals, temporal incoherent signals, or spatiotemporally incoherent signals. For instance, such data can be acquired by varying acquisition parameters from one TR period to the next, which creates a time series of signals with varying contrast. Using this series of varied sequence blocks simultaneously produces different signal evolutions in different resonant species to which RF energy is applied.

As an example, data are acquired using a pulse sequence where effectuating the pulse sequence includes controlling an NMR apparatus (e.g., an MRI system) to apply RF energy to a volume in an object being imaged. The volume may contain one or more resonant species, such as tissue, fat, water, hydrogen, and prosthetics.

The RF energy may be applied in a series of variable sequence blocks. Sequence blocks may vary in a number of parameters including, but not limited to, echo time, flip angle, phase encoding, diffusion encoding, flow encoding, RF pulse amplitude, RF pulse phase, number of RF pulses, type of gradient applied between an excitation portion of a sequence block and a readout portion of a sequence block, number of gradients applied between an excitation portion of a sequence block and a readout portion of a sequence block, type of gradient applied between a readout portion of a sequence block and an excitation portion of a sequence block, number of gradients applied between a readout portion of a sequence block and an excitation portion of a sequence block, type of gradient applied during a readout portion of a sequence block, number of gradients applied during a readout portion of a sequence block, amount of RF spoiling, and amount of gradient spoiling. Depending upon the imaging or clinical need, two, three, four, or more parameters may vary between sequence blocks. The number of parameters varied between sequence blocks may itself vary. For example, a first sequence block may differ from a second sequence block in five parameters, the second sequence block may differ from a third sequence block in seven parameters, the third sequence block may differ from a fourth sequence block in two parameters, and so on. One skilled in the art will appreciate that there are a very-large number of series of sequence blocks that can be created by varying this large number of parameters. A series of sequence blocks can be crafted so that the series have different amounts (e.g., 1%, 2%, 5%, 10%, 50%, 99%, 100%) of unique sequence blocks as defined by their varied parameters. A series of sequence blocks may include more than ten, more than one hundred, more than one thousand, more than ten thousand, and more than one hundred thousand sequence blocks. In one example, the only difference between consecutive sequence blocks may be the number or parameters of excitation pulses.

Regardless of the particular imaging parameters that are varied or the number or type of sequence blocks, the RF energy applied during a sequence block is configured to cause different individual resonant species to simultaneously produce individual NMR signals. Unlike conventional imaging techniques, in an MRF pulse sequence, at least one member of the series of variable sequence blocks will differ from at least one other member of the series of variable sequence blocks in at least N sequence block parameters, where N is an integer greater than one. One skilled in the art will appreciate that the signal content of a signal evolution may vary directly with N. Thus, as more parameters are varied, a potentially richer signal is retrieved. Conventionally, a signal that depends on a single parameter is desired and required to facilitate imaging. Here, acquiring signals with greater information content facilitates producing more distinct, and thus more matchable, signal evolutions.

Figure 2A:
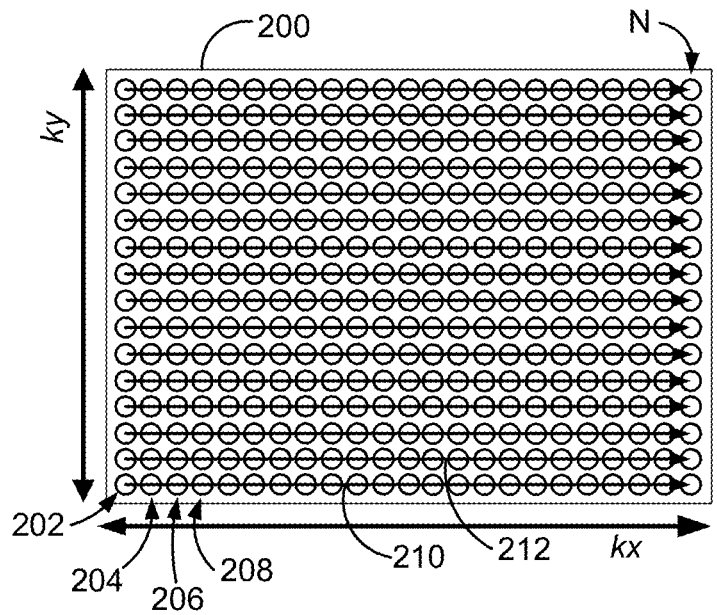
FIG. 2A is a non-limiting example graph of a k-space Cartesian coordinate system formed with equally-spaced sampling points to be acquired sequentially.

FIG. 2A provides an illustration of k-space 200 along the kx axis and ky-axis. In this regard, a Cartesian coordinate system is formed with equally-spaced sampling points 202, 204, 206, 208 . . . N forming a grid. In traditional Cartesian sampling of k-space 200, sampling is performed in a locally sequential pattern (i.e., from 202 to 204 to 206 to 208 . . . ) along arrow 210. The sampling strategy is both locally sequential along a line in k-space given by arrow 210, but also often sequential between rows, as it proceed from the row given by arrow 210 to the arrow given by 212. Each line in k-space is sampled until point N is reached. In this way, each subsequent sampling line in k-space is sequential and within each line the sampling is local or adjacent to a prior sample. Sampling does not move between lines until an entire line is sampled.

Figure 2B:
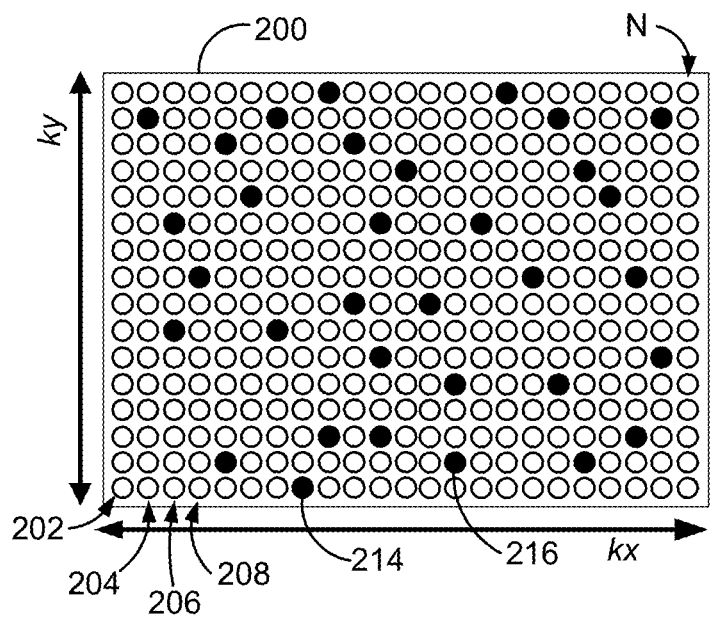
FIG. 2B is a non-limiting example graph of a k-space Cartesian coordinate system with non-locally sequential sampling.

As will be described, the present disclosure provides an MRF framework for acquisition of MRF data based on non-locally sequential and/or non-sequential sampling of k-space in a manner that is designed to have the points sampled or arranged about a Cartesian orientation or selected from a Cartesian grid. In fact, as will described, the present disclosure provides systems and methods where sampling is not bound by being locally sequential within a line, being sequential between lines, or even being sequential between entire Cartesian grids. That is, the systems and methods provided herein allow for sampling irrespective of the locality of the prior sample or subsequent sample in a line or between lines in a Cartesian grid, but also irrespective of the Cartesian grid defined by a given echo or set of echoes in time Specifically, referring to FIG. 2B, the illustration of k-space 200 along the kx-axis and the ky-axis is provided again. However, in this sampling strategy, the Cartesian grid of equally spaced sampling points is present, but sampling does not follow a sequential or local orientation. That is, sample points 202, 204, 206, and 208 have not been sampled, but sample points 214 and 216 have been sampled, as illustrated by the filled state of the sample points 214, 216. Thus, as used herein, non-local or non-sequential sampling of a Cartesian grid or orientation refers to sampling in a manner that does not sample adjacent points in the Cartesian grid, or may provide no preferential sampling priority based on locality or sequence based on locality. In some configurations, the sampling may also be conceptualized as being pseudo-random or random, however, a "pattern" or other strategy, even those that appear as "random" may be utilized. Adjacent points in the Cartesian grid may eventually be sampled as the process continues, or adjacent points may be sampled sequentially. Non-local or pseudo-random sampling can achieve isotropic high-resolution T1, T2 and off-resonance quantification. In some configurations, the acquisition method may include temporal low-rank and subspace modeling to achieve T1, T2 and off-resonance quantification using the MRF framework.

Compared to existing MRF methods based on non-Cartesian sampling patterns such as described with respect to FIG. 2A, the proposed systems and methods provide a flexible sampling framework that is less susceptible to imperfections of the imaging gradients and off-resonance effects. That is, the use of a Cartesian-based readout architecture allows for acquisition times that are shorter than traditional MRF sampling strategies, such as spiral readouts, and reduces the blurring artifacts that are encountered due to off-resonance effects. Thus, the present disclosure provides a robust and high-resolution isotropic MRF method for use in imaging, such as in brain, musculoskeletal, abdominal imaging, and the like.

Figure 3:
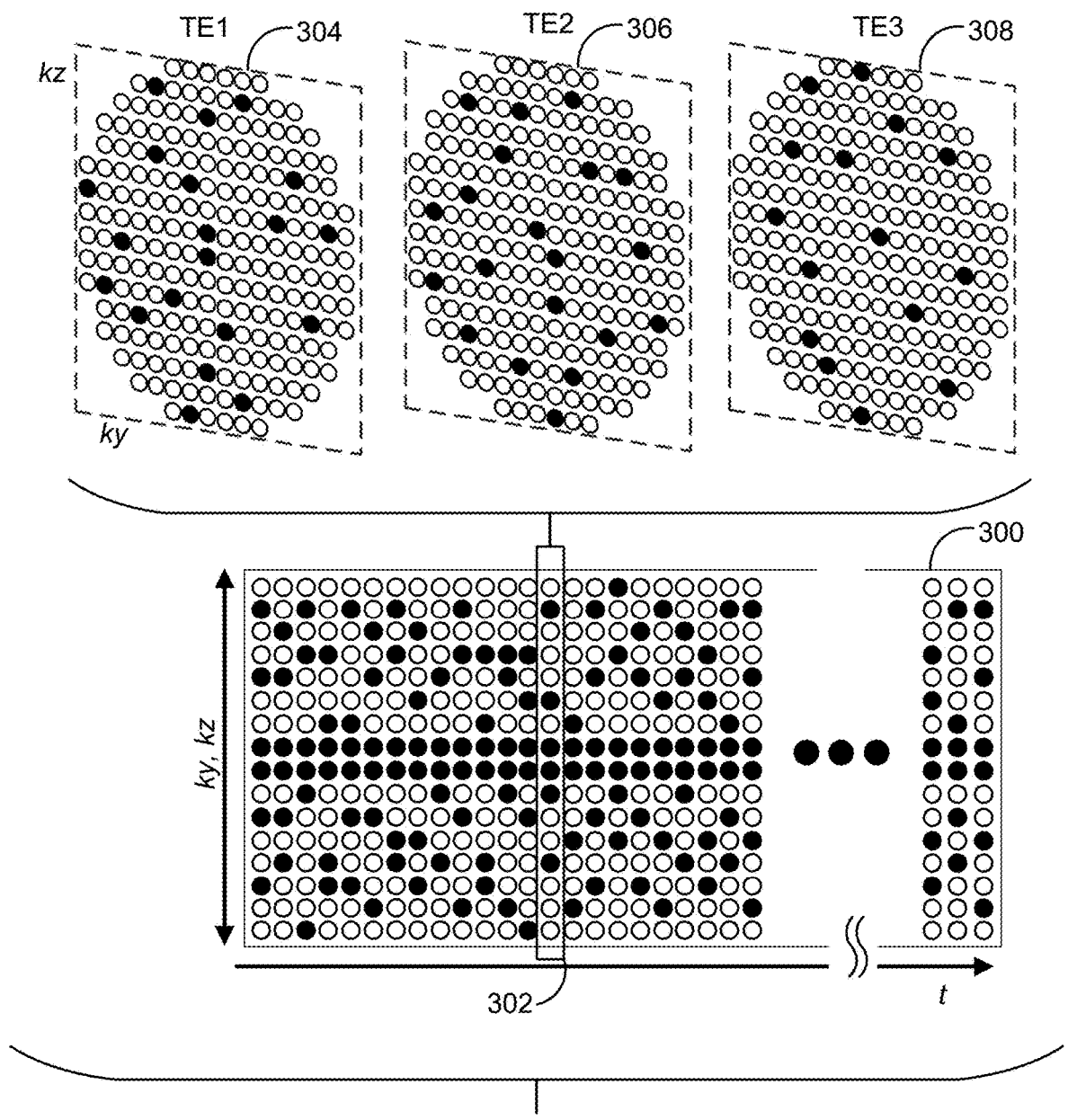
FIG. 3 is another non-limiting example of sampling a k-space Cartesian coordinate system with non-locally sequential sampling strategy that spans across multiple sequence blocks.

The sampling strategies may be extended to more than 2D grids. Referring to FIG. 3, a non-limiting example of a non-local or non-sequential k-space sampling strategy applied to a Cartesian architecture, in accordance with the present disclosure, is shown. In this non-limiting example, a Cartesian grid or architecture of k-space is formed into an array forming a time point matrix 300 along a ky, kz direction over time. In this way, the Cartesian architecture 300 illustrates 4D k-t sampling patterns. For a given time point 302, a corresponding Cartesian grid may be highly undersampled with a non-local or pseudo-random sampling pattern. The readout at each time point may be segmented into a plurality of echo times, such as with three echo times as shown for first echo time 304, second echo time 306, and third echo time 308. Segmenting the time point into a plurality of echo times may enhance the sensitivity of the readout to off-resonance effects, such as a fast imaging with steady state precession (FISP) readout. This non-limiting example sampling pattern for time point matrix 300 is assembled from data acquired from multiple time points.

The pulse sequence used to acquire the samples may apply members of the series of variable sequence blocks accordingly to undersample the object at an undersampling rate, R. In different situations, the undersampling rate, R, may be, for example, two, four, or greater.

In one non-limiting example with variable echo times, a method according to the present disclosure encodes the off-resonance effects in a FISP readout, which has the potential to achieve chemical shift encoding for water-fat separation and to measure T2*. The method provides a robust and high resolution isotropic MRF, which may be used in any imaging application, such as musculoskeletal, abdominal imaging, and the like.

Figure 4:
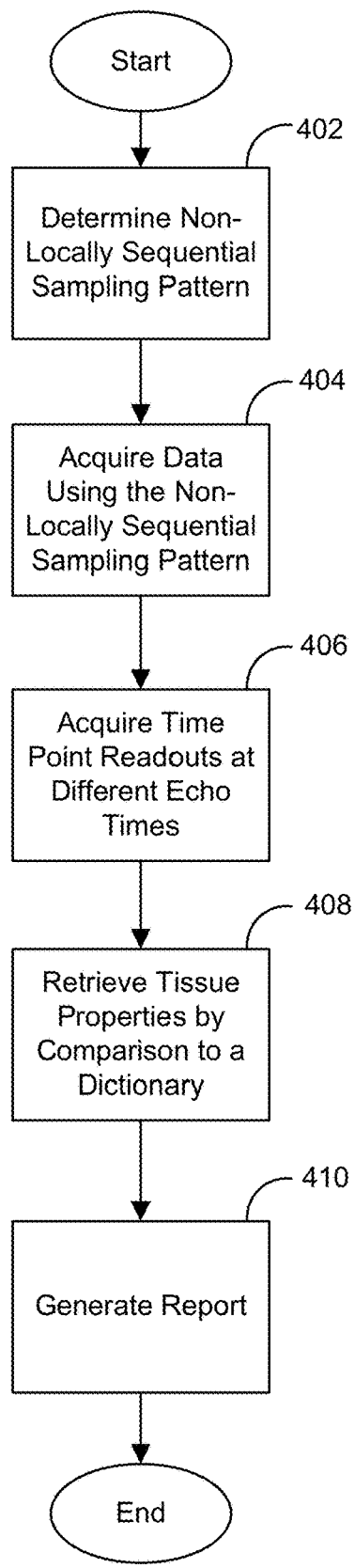
FIG. 4 is a flow chart with non-limiting example steps for a method for MRF data acquisition according to the present disclosure.

Referring to FIG. 4, a flow chart is provided that sets forth some non-limiting example steps for a method for MRF process in accordance with the present disclosure. At process block 402, a non-local, non-sequential or pseudo-random sampling pattern is determined. In one non-limiting example, the sampling pattern is a poisson-disc sampling pattern in a Cartesian acquisition. The use of the above-described non-locally sequential sampling patterns allows for undersampling k-space data in an MRI or MRF data acquisition. At process block 404, data is acquired using the non-locally sequential sampling pattern. In one non-limiting example, 4D k-t space data may be acquired using the sampling strategy. To facilitate off-resonance encoding, time point readouts at different echo times may be acquired at step 406. At process block 408, the acquired data is compared to a dictionary. Finally, at process block 410, a report, which may include a map or image, is generated or displayed to the user.

In some configurations, the non-locally sequential acquisition may be a 3D Cartesian MRF-FISP2 acquisition with a Poisson-disc sampling pattern that acquires 4-D k-t space data. Multiple time points may be acquired, such as a total of five hundred time points as a non-limiting example. Time points may be acquired with varied flip angles. A constant TR, such as a TR of 5.68 ms, may be used in one non-limiting example. Each time point may be highly undersampled. To encode off-resonance, such as in a FISP sequence, the ky-kz readouts of each time point may be segmented to be acquired at different echo times, while flip angle and repetition time may be the same. In one non-limiting example, three different echo times may be used for each time point. One skilled in the art will appreciate that any number of echo times may be used.

In some configurations, generating the report at process block 410 may include performing a low-rank reconstruction to create an image of each time point first, and then tissue properties may be retrieved by taking the maximum of the inner product between the reconstructed image and the dictionary. The low-rank reconstruction may take a variety of forms. In one non-limiting example, a low-rank reconstruction for T2-shuffling may be used. The reconstruction may take on a form such as:

$$\min_\alpha \frac{1}{2}\|y - EU_k\alpha\|_2^2 + \lambda \sum_r \|R_r(\alpha)\|; \tag{5}$$

where E is the encoding matrix that contains sampling masks and coil sensitives, $U_k$ is the subspace learned from the dictionary by using singular-value decomposition (SVD), $\alpha = U_k^H x$ represents the compressed low-rank images, and $$\sum_r \|R_r(\alpha)\|_*$$

is a local low-rank regularization on low-rank images with block size r. Implementation may be with any appropriate software, such as Matlab using the BART toolbox, and the like.

Figure 5:
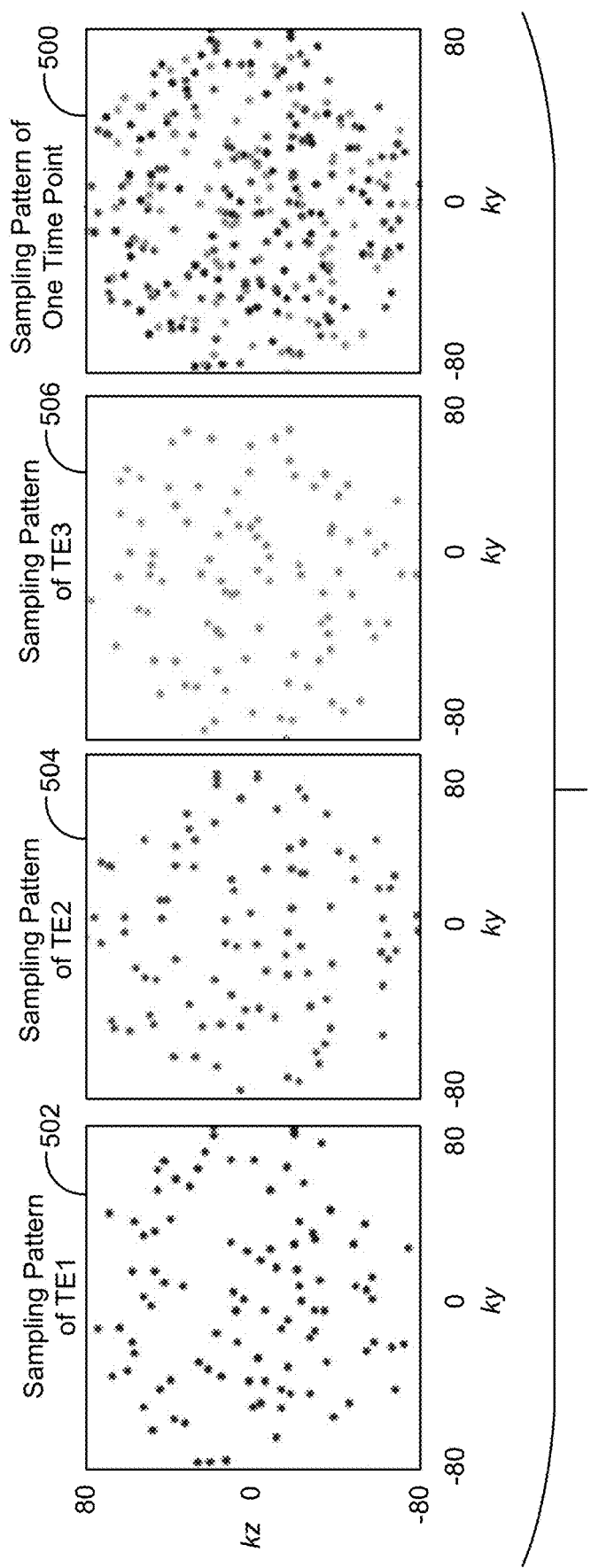
FIG. 5 is also a non-limiting example graph of k-space data sampling according to the present disclosure.

Referring to FIG. 5, non-limiting example graphs of k-space data sampling according to the present disclosure are shown. The sampling pattern of one time point 500 may be segmented into different echo times, as discussed above. Non-limiting example sampling patterns are shown for a first echo time 502, second echo time 504, and third echo time 506.

In one non-limiting example, the block size r was selected to be 8 and the reconstruction was solved by FISTA with λ=0.01 of the maximum signal intensity of the low-rank images. A dictionary containing a representative subset of potential signal evolutions was calculated using a Bloch equation simulation. The dictionary had 409,460 entries with T1 of 10-3000 ms, T2 of 1-800 ms, and off-resonance of −500-500 Hz. The dictionary was compressed into the temporal subspace by taking the first k=16 singular vectors of SVD. A 3T scanner was used with a 20-channel head receiver array for the phantom and the brain and a 15-channel TX/RX knee coil for the knee.

Data was acquired for time points of a matrix size of 192×192 and selected to be a pseudorandom 3D Cartesian MRF-FISP2 acquisition with a Poisson-disc sampling pattern as described above to acquire 4-D k-t space data. The segment at each echo time was acquired with 96 readout lines, leading to an undersampling factor of R=192×192/96=384. Example acquisition parameter sizes are shown in table 1.

TABLE 1

Non-limiting Example Acquisition Parameters

| | NIST/ISMRM Phantom | Brain | Knee |
|---|---|---|---|
| FOV (mm³) | 220 × 220 × 220 | 192 × 192 × 192 | 160 × 160 × 160 |
| Matrix Size | 192 × 192 × 192 | 192 × 192 × 192 | 160 × 160 × 160 |
| TR (ms) | | 5.68 | |
| TEs (ms) | | 2.11, 2.88, 3.65 | |
| Readout Lines per Echo | 96 | 96 | 66 |
| Acquisition Time (mins) | 16 | 16 | 11 |

Correlation curves were generated that compare T1 and T2 values derived from the methods of the present disclosure to the standard values reported by the NIST. The correlations curves demonstrate that the MRF measurements are in good agreement with reference values. In vivo T1, T2, off-resonance and proton density maps in brain were also acquired. The T1 and T2 values were 774±55.4 ms and 45±4.1 ms in white matter, 1236.7±96.9 and 70±9.1 ms in gray matter, which were in the range of previous reported values from 3D spiral MRF-FISP method. In vivo T1, T2, off-resonance and proton density maps of the knee were also acquired. The T1 and T2 values were 350±10 ms and 143±5.8 ms in bone marrow fat, 1230±61 ms and 37±7.1 ms in cartilage, and 1370±61 ms and 40±4.5 ms.

The present disclosure has described one or more preferred embodiments, and it should be appreciated that many equivalents, alternatives, variations, and modifications, aside from those expressly stated, are possible and within the scope of the invention.

The invention claimed is:

1. A method for magnetic resonance fingerprinting (MRF) data acquisition using a computer system comprising:
    a) determining a non-locally sequential sampling pattern for a Cartesian grid of k-space;
    b) performing a series of sequence blocks using acquisition parameters that vary between sequence blocks to acquire MRF data from a subject using the Cartesian grid of k-space and the determined non-locally sequential sampling pattern;
    c) assembling the MRF data into a series of signal evolutions;
    d) comparing the series of signal evolutions to a dictionary of known signal evolutions to determine tissue properties of the subject; and
    e) generating a report indicating the tissue properties of the subject.

2. The method of claim 1, further comprising segmenting each point in the non-locally sequential sampling pattern into a plurality of echo times to control off-resonance effects.

3. The method of claim 1, wherein determining the non-locally sequential sampling pattern includes selecting a Poisson-disc sampling pattern.

4. The method of claim 1, wherein the non-locally sequential sampling pattern is a pseudorandom sampling pattern.

5. The method of claim 1, further comprising using the computer system to reconstruct an undersampled image of the subject using a low-rank reconstruction.

6. The method of claim 5, wherein the low-rank reconstruction is of the form:

$$\min_\alpha \frac{1}{2}\|y - EU_k\alpha\|_2^2 + \lambda \sum_r \|R_r(\alpha)\|$$

where E represents the encoding matrix that contains sampling masks and coil sensitives, $U_k$ represents a subspace learned from the dictionary by using a singular-value decomposition (SVD), $\alpha = U_k^H x$ represents compressed low-rank images, and $$\sum_r \|R_r(\alpha)\|_*$$

represents a local low-rank regularization on low-rank images with block size r.

7. The method of claim 1, wherein comparing the series of signal evolutions to a dictionary of known signal evolutions includes reconstructing an image of the subject form the MRF data and determining a maximum of an inner product between the image of the subject and the dictionary.

8. A magnetic resonance fingerprinting (MRF) system comprising:
    a magnet system configured to generate a polarizing magnetic field about at least a portion of a subject;

a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals from the subject using a coil array;

a computer system programmed to:
determine a non-locally sequential sampling pattern for a Cartesian grid of k-space;
control the magnetic gradient system and the RF system to perform a series of sequence blocks using acquisition parameters that vary between sequence blocks to acquire MRF data from a subject using the Cartesian grid of k-space and the non-locally sequential sampling pattern;
assemble the MRF data into a series of signal evolutions;
compare the series of signal evolutions to a dictionary of known signal evolutions to determine tissue properties of the subject; and
generate a report indicating the tissue properties of the subject.

9. The system of claim 8, wherein the computer system is further programmed to segment each point in the non-locally sequential sampling pattern into a plurality of echo times to control off-resonance effects.

10. The system of claim 8, wherein the computer system is further configured to select a Poisson-disc sampling pattern to determine the non-locally sequential sampling pattern.

11. The system of claim 8, wherein the non-locally sequential sampling pattern is a pseudorandom sampling pattern.

12. The system of claim 1, wherein the computer system is further configured to reconstruct an undersampled image of the subject using a low-rank reconstruction.

13. The system of claim 12, wherein the low-rank reconstruction is of the form:

$$\min_\alpha \frac{1}{2}\|y - EU_k\alpha\|_2^2 + \lambda \sum_r \|R_r(\alpha)\|$$

where E represents the encoding matrix that contains sampling masks and coil sensitives, $U_k$ represents a subspace learned from the dictionary by using a singular-value decomposition (SVD), $\alpha = U_k^H x$ represents compressed low-rank images, and $$\sum_r \|R_r(\alpha)\|_*$$

represents a local low-rank regularization on low-rank images with block size r.

14. The system of claim 1, wherein comparing the series of signal evolutions to a dictionary of known signal evolutions includes reconstructing an image of the subject form the MRF data and wherein the computer system is further configured to determine a maximum of an inner product between the image of the subject and the dictionary.

* * * * *